United States Patent
Brotzge et al.

(10) Patent No.: US 10,123,859 B2
(45) Date of Patent: Nov. 13, 2018

(54) FIRING FURNACE AND PRESS FURNACE

(71) Applicant: Ivoclar Vivadent AG, Schaan (LI)

(72) Inventors: Michael Brotzge, Koblach (AT); Johannes Lorünser, Bludenz (AT)

(73) Assignee: Ivoclar Vivadent AG, Schaan (LI)

( * ) Notice: Subject to any disclaimer, the term of this patent is extended or adjusted under 35 U.S.C. 154(b) by 609 days.

(21) Appl. No.: 14/353,796

(22) PCT Filed: Oct. 10, 2013

(86) PCT No.: PCT/EP2013/071112
§ 371 (c)(1),
(2) Date: Apr. 24, 2014

(87) PCT Pub. No.: WO2014/063922
PCT Pub. Date: May 1, 2014

(65) Prior Publication Data
US 2016/0220338 A1 Aug. 4, 2016

(30) Foreign Application Priority Data
Oct. 24, 2012 (EP) .................................... 12189816

(51) Int. Cl.
*F27B 5/14* (2006.01)
*A61C 3/00* (2006.01)
(Continued)

(52) U.S. Cl.
CPC ................ *A61C 13/20* (2013.01); *F27B 5/06* (2013.01); *F27B 17/025* (2013.01); *F27D 19/00* (2013.01); *H05B 3/026* (2013.01)

(58) Field of Classification Search
CPC ... A61C 13/20; A61C 3/00; F27B 5/00; F27B 5/06; F27B 5/10; F27B 5/18; F27B 17/025; F27B 5/14; F27D 19/00; H05B 3/026
(Continued)

(56) References Cited

U.S. PATENT DOCUMENTS 5,072,360 A 12/1991 Knorpp et al.
6,198,080 B1 * 3/2001 Rice ........................ F24C 7/082
219/412
(Continued)

FOREIGN PATENT DOCUMENTS

DE 3831539 A1 3/1990
DE 4019395 A1 12/1991
(Continued)

*Primary Examiner* — Michael G Hoang
(74) *Attorney, Agent, or Firm* — Ann M. Knab; Thad McMurray

(57) ABSTRACT

The invention relates to a firing furnace or press furnace for dental restoration parts, having a control device for the control of the furnace on the basis of at least one firing/press program; a display device, at least for displaying operating instructions based on symbolic representations; an input device, at least for selecting a firing/press program; wherein the control device is configured to be able to switch the furnace after selection of a control program to a security mode in which it displays one or several operating instructions and in which the input of firing or press parameters of the control program and/or the selection of a firing or press program is disabled.

16 Claims, 4 Drawing Sheets

(51) Int. Cl.
*A61C 13/20* (2006.01)
*F27B 17/02* (2006.01)
*F27D 19/00* (2006.01)
*F27B 5/06* (2006.01)
*H05B 3/02* (2006.01)

(58) Field of Classification Search
USPC ......... 432/120; 110/191, 193; 219/390, 391, 219/392, 406, 420; 433/32, 229
See application file for complete search history.

(56) References Cited

U.S. PATENT DOCUMENTS

| | | |
|---|---|---|
| 7,001,778 B2 | 2/2006 | Karasawa et al. |
| 2005/0175949 A1 | 8/2005 | Grunenfelder et al. |
| 2009/0117504 A1 | 5/2009 | Grunenfelder |

FOREIGN PATENT DOCUMENTS

| | | |
|---|---|---|
| DE | 102004026107 A1 | 12/2005 |
| JP | 1989155871 A | 6/1989 |
| JP | 1990116366 A | 5/1990 |
| JP | 1993304794 A | 11/1993 |
| JP | 2000329477 A | 11/2000 |
| RU | 2063727 C1 | 7/1996 |

* cited by examiner

FIRING FURNACE AND PRESS FURNACE

CROSS-REFERENCE TO RELATED APPLICATIONS

This application is a National Stage application of International patent application PCT/EP2013/071112 filed on Oct. 10, 2013, which claims priority to European patent application No. 12189816.7 filed on Oct. 24, 2012, the disclosures of which are incorporated herein by reference in their entirety.

The invention relates to a firing or press furnace for dental restorations according to the preamble of claim 1.

Dental furnaces of this kind for firing and possibly pressing dental restoration parts have long been known. In dental furnaces of this kind a dental restoration part or a plurality of dental restoration parts is subjected to a firing process or press process, namely in a program-controlled manner according to predefined temperature and possibly press profiles.

The quality of the dental restoration parts produced depends to a large extent on the accurate compliance with the predetermined parameters which are adapted to the existing dental restoration material during the firing and possibly press process. They include the temperature profile to be complied with but also, for instance, the existing pressure conditions during the firing cycle.

Such dental restoration parts include dental restoration parts made from a plastic, metal, composite but in particular also from a ceramic material.

The materials to be processed, the size but also the number and shape of the dental restoration parts to be produced simultaneously determine, among other things, the total heat capacity of the dental restoration parts to be processed. This can result in the need to adapt the heating capacity, and for this purpose, via an input device of these firing or press furnaces different processing programs can be activated in which ideal operating parameters for the corresponding framework conditions (material, size, etc.) are stored. The activation and starting of a suitable processing program aims at a firing process which achieves an ideal product quality.

Dental furnaces of this type substantially comprise a furnace base in which the dental restoration parts to be fired are received, possibly in a muffle, a furnace hood in which apart from the thermal insulation the heating device (e.g. electric heating coils) is also received in most cases, and a control device comprising a display and input device connected thereto. The control device further comprises a storage device in which the processing programs are stored. The input device itself can be partially combined with the display device in the form of a touch screen and can further comprise dedicated keys or keys which can be assigned different functions via the display ("soft keys").

A dental furnace of this kind is, for instance, described in DE 197 54 077 B4. A display device can display parameters both numerically and as differently colored curves which can be overlapped with each other. Inputs are possible via keys whereby a firing program can be modified, if necessary.

Basically, the programming of such a furnace offers the simple and effective possibility of carrying out a correct setting of the necessary parameters by an experienced specialist or even on the furnace manufacturer's premises and of operating the furnace (charging, starting of the firing program, etc.) by a less experienced operator as no detailed knowledge is necessary for this purpose.

Surprisingly, large laboratories are experiencing quality problems when using program controlled dental furnaces at present.

In order to counteract these problems attempts have been made to simplify the menus of dental furnaces; however, this can also involve a more complicated programming of these furnaces which is basically desired, as a matter of fact, to also be able to automate more complex processing programs. Nevertheless, the aforementioned quality problems, such as clearly visible variations in the coloring of the readily fired dental restoration parts, could not be eliminated up to now.

Therefore, the invention is based on the task of providing a dental furnace according to the preamble of claim 1, which is used to simplify the work in dental laboratories even regarding complex requirements and high quality expectations, without complicating the operation of the dental furnaces beyond the extent relevant in practice.

This task is inventively solved by claim 1. Advantageous developments may be taken from the subclaims.

The basic operation of a firing furnace of this type, such as opening the furnace hood, closing the furnace after charging it with the objects to be fired and starting the furnace by an authorized superior according to the material to be processed and the further framework conditions (size of the dental parts, etc.) of the pre-set processing program, can be inventively carried out without further ado by a less qualified operator.

The provision of a "secure" operating mode in a dental furnace according to the present invention and of the related severe restriction of menu functions accessible by an employee who is not qualified for programming the furnace surprisingly results in a considerably simplified operation while at the same time the security in the operation of the furnace is increased significantly.

In this respect, in the inventive security mode, the less qualified operator is only allowed to, for instance, open the furnace in the standby mode (for charging it), to start a processing program previously selected by a foreman and to re-open the furnace when the program is finished (wherein at this point the furnace is in the standby mode again).

However, access to the programming of the inventive furnace and also, for instance, an abortion of the firing program is disabled for such an operator in order to be able to ensure the desired quality of the readily fired dental parts.

Misuse, inadmissible abortion of the firing cycle or changes to the stored parameters in the programs which are made in an inadmissibly deliberate way, but in good faith via corresponding menu functions by less qualified employees are thus practically not possible anymore.

With increasing cost pressure the number of less experienced or not specifically trained workers who substantially carry out the actual operation of the furnaces rises in the production process, and, in contrast, the number of experienced (and more expensive) specialists decreases.

Altered program parameters or even a program abort would lead to a worse quality of the fired products or render them unusable in the worst case. Furthermore, additional costs for material, wage and energy can be caused unnecessarily besides the fact that the requested dental parts may possibly not be finished and delivered to the client within the deadline. According to the invention, this can be prevented effectively using the provided security mode.

A further development which can be observed more and more often in this connection is the employment of foreign-language employees in the production process which can additionally lead to problems of understanding the operating language used in the furnaces.

According to the invention it is especially favorable that any language problems of foreign-language employees can be responded to, to a certain extent, by the use of symbols and pictograms both on the control elements to be used and in the menus. The use of meaningful symbols also facilitates the operation for linguistically qualified employees and the danger of misuse is reduced.

In this respect, in an inventively favorable manner these dental furnaces are provided with a so-called security mode which preempts unauthorized changes to the processing programs which are stored in the furnace by refusing access to the programming functions in the inventive dental furnace in the security mode. Moreover, further functions, such as "Stop" (abort) or "Open the Furnace" are not selectable while a processing program (which has already been started) is running and the cycle has not been completed fully.

In an inventively favorable manner, the display device located on the inventive furnace can display, for instance, only the number of the furnace, the furnace temperature, the remaining time until the started processing program has been completed entirely, the type of the operating mode selected as well as some information on the selected program which is of interest for an experienced technician, but which is, however, of relatively small importance for less qualified operators.

In this way, in the security mode (before program start-up) only the functions "Open Furnace", the subsequent "Close Furnace" and afterwards "Start" (the processing program) are enabled. After starting the processing program, the function "Open Furnace" is additionally disabled as opening the furnace during the running program would very likely render the product unusable. In this respect, within the program in this security mode it is impossible to select a processing program or change parameters.

The operation for an operator of the furnace who does not know the operation language of the furnace can be additionally simplified by means of an additional representation of corresponding symbols or pictograms in the display or on possibly available control keys.

By entering an authorization (ID, pass word, etc.) at the inventive furnace, an employee superior to the low-skilled operator (who is not authorized to make changes to parameters in the programs either) has the opportunity to select a processing program in a priority operating mode and then to switch the furnace into security mode.

In addition to both previously mentioned modes with highest security (security mode) and lower security (priority operating mode), at the dental furnace, by using suitable authorization methods (entry of an ID or a pass word, card reader or the like) a programming mode known per se can be activated which allows unlimited access to the programs stored in the dental furnace. In the programming mode programs can thus be modified (parameters changed), created from scratch and also deleted. In doing so, entering the corresponding parameters and values takes place in an inventively favorable manner via the touch screen. Furthermore, for instance the loading of prepared programs can also take place using a USB flash drive, LAN connection or any other suitable means. In any case, after successfully programming the dental furnace, it is set to security mode again to prevent undesired changes to the program.

In an inventively favorable manner this switching on of the security mode can also take place automatically after expiration of an adjustable period of time.

In a further advantageous embodiment of the invention it is provided that the furnace comprises a programming mode in which changes to at least one program, reprogramming of at least one program, a change to at least the sequence of the stored programs, a change to the priorization of the stored programs and/or the authorization of users for the selection of the given programs can be produced, changed or deleted.

In a further advantageous embodiment of the invention it is provided that the input device is integrated in the display device in a way know per se, or coupled to it, and in particular comprises a touch screen facilitating the operation of the furnace at least in the security mode.

In a further advantageous embodiment of the invention it is provided that the furnace can be transferred from the programming mode to the security mode upon actuation of one single control panel or any other single control function.

In a further advantageous embodiment of the invention it is provided that the furnace can be transferred from the security mode to the programming mode by entering a code or a hidden control function or via remote control.

In a further advantageous embodiment of the invention it is provided that in the security mode firing programs and/or press programs can be selected and executed depending on the design of the furnace as a firing furnace or press furnace.

In a further advantageous embodiment of the invention it is provided that the input device and/or the display device comprises a field which is provided with "Start" or a corresponding symbol, wherein the start field starts a preselected program in the security mode.

In a further advantageous embodiment of the invention it is provided that the display device and/or the input device comprises a stop field or a corresponding function, possibly as a symbol, which is active both in the programming mode and in the security mode and terminates the press program or firing program which has already been started.

In a further advantageous embodiment of the invention it is provided that in the security mode, once a program has been started, a signal field and/or an acoustic signal, for instance a buzzing sound, is active when a press program or a firing program, depending on the type of firing furnace or press furnace, has been started and is running.

In a further advantageous embodiment of the invention it is provided that at the end of a program in the security mode the end of program is signaled by an optical and/or acoustic signal known per se and/or the furnace enters into an energy saver mode automatically or manually.

In a further advantageous embodiment of the invention it is provided that the display device and/or the input device comprises a field which is associated with the programming and is in particular designated by "P", which field, in the security mode, allows to select the program out of the programs available to the user and, in the programming mode, facilitates to freely program programs, in particular to change, set up and delete programs.

In a further advantageous embodiment of the invention it is provided that the display device and/or the input device comprises a "Home" field and/or a field for entering a code which is active and controllable both in the programming mode and in particular in the security mode and which is used to reset the furnace to an initial state in which free programming in the programming mode or free operation in the security mode is possible.

In a further advantageous embodiment of the invention it is provided that the display device and/or input device comprises at least one symbol field for opening the furnace and at least one symbol field for closing the furnace which fields are active when no firing/press program is running.

In a further advantageous embodiment of the invention it is provided that in addition to the security mode and the programming mode a priority operating mode is selectable, in particular by activating a selection field from the programming mode and/or by entering a code from the security mode in which the user can set further parameters, in particular change firing parameters and/or press parameters of programs temporarily, beyond the functions of the security mode.

In a further advantageous embodiment of the invention it is provided that a high security mode is selectable in which only one single firing/press program can be started and which can be left for the security mode, the priority operating mode and/or the programming mode by entering a code.

Further advantages, details and features of several exemplary embodiments may be taken from the following description of the invention, in which.

Figure 1:
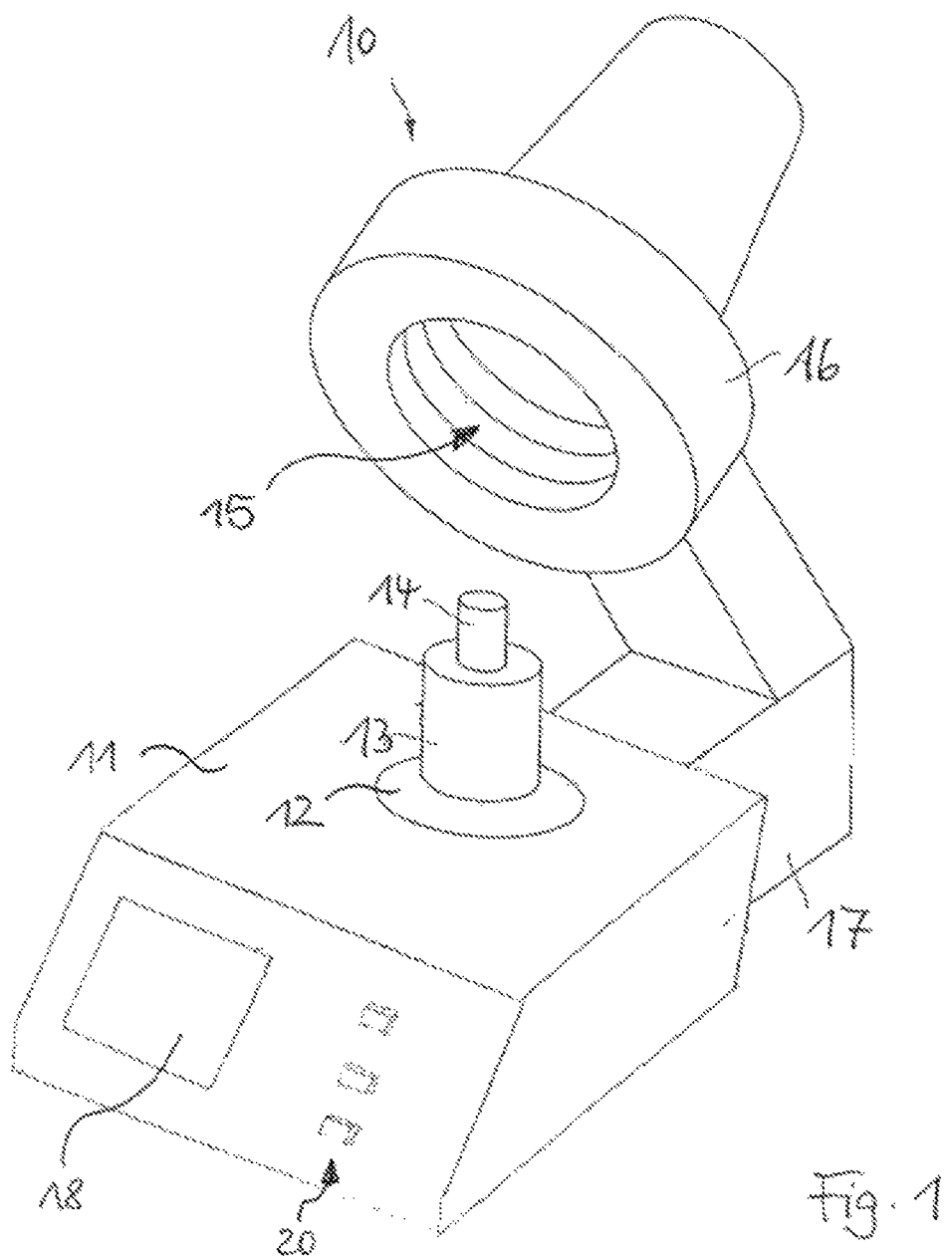
FIG. 1 shows a schematic view of a dental furnace according to the state of the art.

A dental furnace 10 comprises a furnace base 11 with a combustion chamber floor 12 which is intended to receive the objects to be burned, for instance a muffle 13 (illustrated here with an inserted blank 14). For the firing process, the objects to be burned are received in a combustion chamber 15 which is indicated only schematically in FIG. 1 and which is configured in the furnace hood 16 which is connected to the furnace base via a joint 17. If the inventive dental furnace 10 involves a press furnace, it is additionally provided with a device, preferably in the furnace hood 16, for pressing the dental material to be processed; however, to provide a better overview this device is not illustrated herein.

The dental furnace 10 further comprises a display device 18 and keys 20 which interact with a control device comprising a storage device (not illustrated either).

In the condition illustrated in FIG. 1 the furnace hood 16 (including the combustion chamber 15) is lifted such that the objects to be burned can be inserted.

Figure 2:
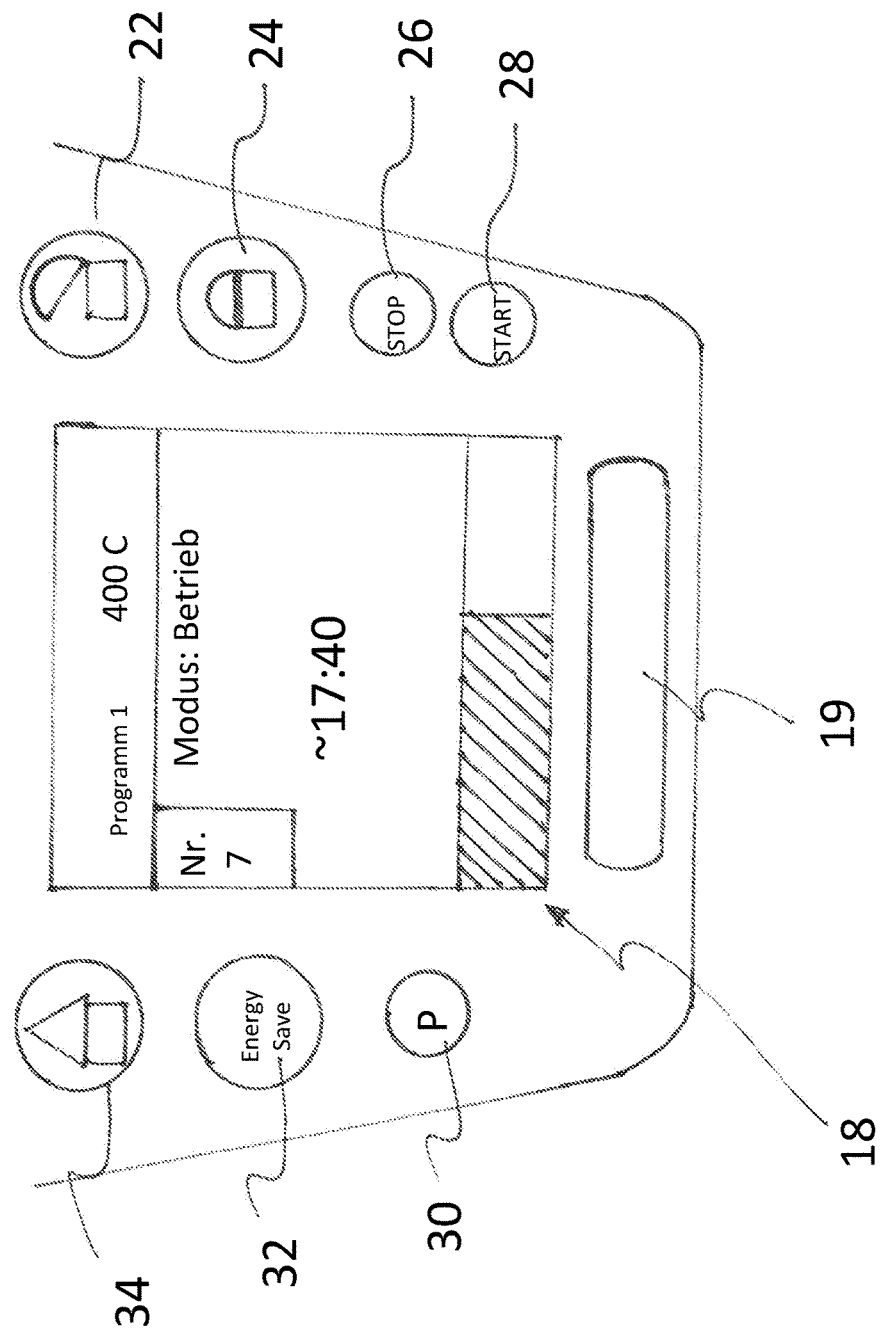
FIG. 2 shows a schematic view of the display and input device during operation of the inventive furnace.

FIG. 2 shows the display field of an inventive dental furnace 10 comprising the display 18 and the keys 20 in the operating state of the furnace, i.e. during a running processing program. In an inventively favorable manner the display 18 involves a touch screen which can be used to, for instance, select a processing program but also detailed inputs regarding program parameters etc. in a way known per se.

Centrally in the display device the touch screen 18 is positioned which shows, besides the furnace temperature, the current operating mode, the furnace number, the remaining execution time (illustrated numerically and as a bar), a few more details about the selected program. Below the display 18 a broad illuminated display 19 is disposed, also centrally, which emits red light in the operating mode to signalize that it is not possible to operate the dental furnace during the running program operation.

On the right-hand side of the display 18 there are keys 22 (for "Open Furnace") and 24 ("Close Furnace") as well as keys 26 (for "Stop") and 28 ("Start") which can additionally be color coded, for instance, red for "Stop" and green for "Start".

On the left-hand side of the display 18 there are further keys for the programming mode 30 ("P"), 32 (for an energy saver mode) as well as key 34 ("Home").

As in the security mode the touch screen is only supposed to show information but not to receive entries, the touch sensitivity is deactivated in this mode.

According to the invention in the operating mode, i.e. during the running processing program, all keys (22, 24, 26, 28) on the right-hand side are disabled as the furnace must not be opened and the program must not be terminated (canceled).

Via key 30 ("P") the programming mode can be selected which, however, can only be activated inventively in the security mode by entering a suitable authorization. An input can, for instance, take place in a way known per se via a keypad illustrated on the touch screen 18.

The actuation of the "Home" key (34) causes the furnace to be reset into an initial state by the user, i.e. to return to the display of the basic operating parameters (furnace number, temperature, etc.) in the case of the active security mode. By pressing the key "Energy Save" the furnace can further be switched to an energy saver mode during the different parts of the firing cycle in which this function is enabled.

Figure 3:
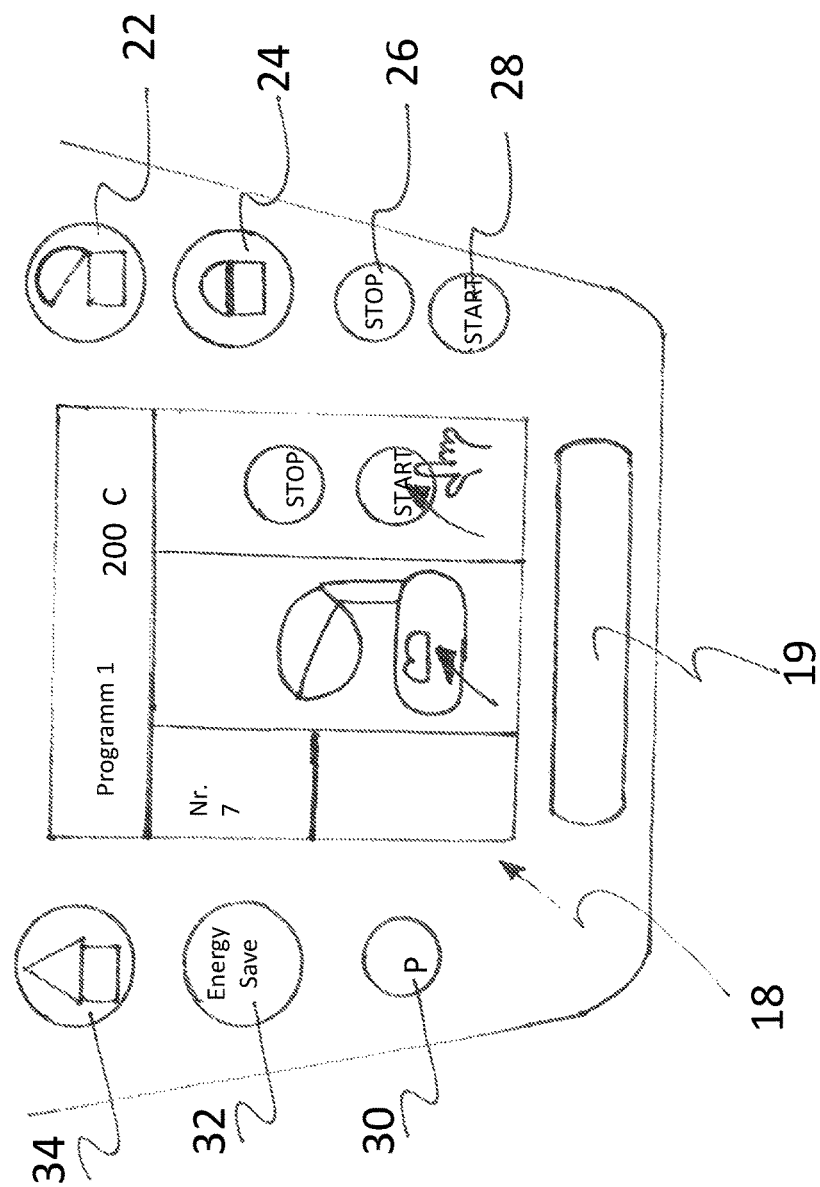
FIG. 3 shows a schematic view of the display and input device according to FIG. 2 with the hood being open in the standby mode of the inventive furnace.

Just like FIG. 2, FIG. 3 shows the display field but here in the standby mode of the furnace with an open furnace hood. In this state the dental furnace can be charged anew which is illustrated using a corresponding image in the display 18. In this case the luminous bar display 19 below the display 18 emits a green light as in this case it is possible to operate the dental furnace. In the bottom right part of the display 18 it is further illustrated symbolically which key needs to be pressed by the user to start the processing program. By pressing the key 26 ("Start") the furnace hood closes automatically and the processing program starts to heat the combustion chamber after the hood has been closed completely.

Figure 4:
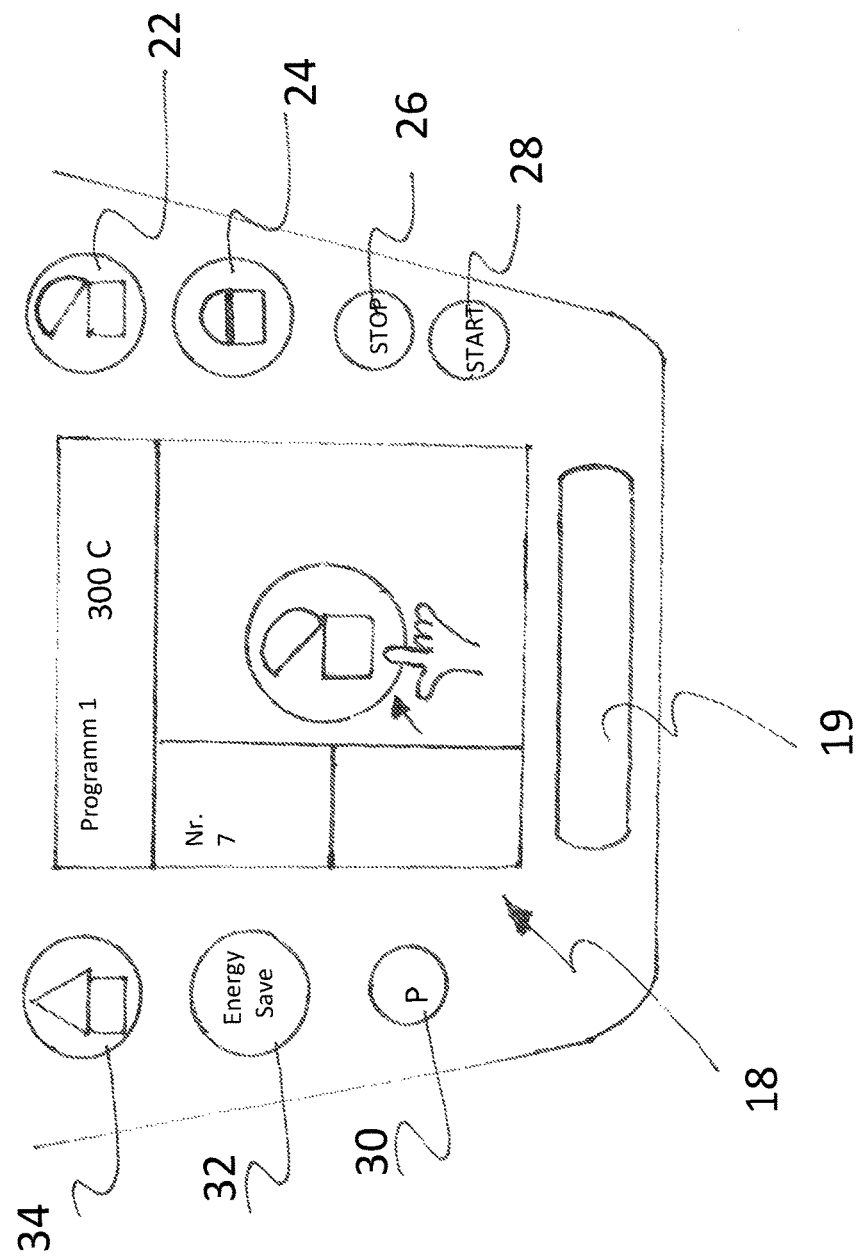
FIG. 4 shows a schematic view of the display and input device according to FIG. 2 with the hood being closed in the standby mode of the inventive furnace.

FIG. 4 further shows the display field in the standby mode of the furnace with the furnace hood being closed, i.e. after the end of the processing program. In this case, the operation of the key 22 ("Open Furnace") is enabled such that the dental restoration part which has been fired completely can be removed from the furnace. In this case, too, this is illustrated using a corresponding image in the display 18, and the luminous bar display 19 emits a green light as it is now possible again to operate the dental furnace.

The invention claimed is:

1. A firing furnace or press furnace for dental restorations, comprising:
   a control device for the control of the firing furnace or press furnace on a basis of at least one firing/press program;
   a display device, at least for displaying operating instructions based on symbolic representations;
   an input device, at least for selecting a firing/press program;
   wherein the control device is configured to be able to switch the firing furnace or press furnace after selection of a control program to a security mode in which the display device displays one or several operating instructions and in which input of firing or press parameters of the control program and/or selection of a firing or press program is disabled, wherein in the security mode, at least one of (i) an open furnace function, (ii) a close furnace function, and (iii) start of a selected firing/press program can be enabled.

2. The firing furnace or press furnace according to claim 1, characterized in that the firing furnace or press furnace comprises a programming mode, wherein the programming mode comprises options for programming and changing programs including changes to at least one program, reprogramming of at least one program, a change to at least a sequence of stored programs, a change to prioritization of the stored programs and/or authorization of users for selection of given programs can be produced, changed or deleted.

3. The firing furnace or press furnace according to claim 1, characterized in that the input device is integrated in the display device or coupled to it, and comprises a touch screen facilitating operation of the firing furnace or press furnace at least in the security mode.

4. The firing furnace or press furnace according to claim 1, characterized in that the firing furnace or press furnace can be transferred from a programming mode to the security mode upon actuation of one single control panel or any other single control function.

5. The firing furnace or press furnace according to claim 1, characterized in that the firing furnace or press furnace can be transferred from the security mode to a programming mode by entering a code or a hidden control function or via remote control.

6. The firing furnace or press furnace according claim 1, characterized in that in the security mode firing programs and/or press programs can be selected and executed depending on the design of the furnace as a firing furnace or press furnace.

7. The firing furnace or press furnace according to claim 1, characterized in that the input device and/or the display device comprises a field which is provided with Start or a corresponding symbol, wherein the Start field starts a preselected program in the security mode.

8. The firing furnace or press furnace according to claim 1, characterized in that the display device and/or the input device comprises a stop field or a corresponding function, as a symbol, which is active both in a programming mode and in the security mode and terminates the press program or firing program which has already been started.

9. The firing furnace or press furnace according to claim 1, characterized in that in the security mode, once a program has been started, a signal field and/or an acoustic signal is active when a press program or a firing program, depending on the type of firing furnace or press furnace, has been started and is running.

10. The firing furnace or press furnace according to claim 1, characterized in that at the end of a program in the security mode, the end of the program is signaled by an optical and/or acoustic signal and/or the firing furnace or press furnace enters into an energy saver mode automatically or manually.

11. The firing furnace or press furnace according to claim 1, characterized in that the display device and/or the input device comprises a field which is associated with programming and is designated by P, wherein the field associated with programming and designated by P when in the security mode, allows to select a program out of programs available to a user and, in a programming mode, facilitates to freely program programs, comprising to change, set up and delete programs.

12. The firing furnace or press furnace according to claim 1, characterized in that the display device and/or the input device comprises a Home button and/or a field for entering a code which is active and controllable both in a programming mode and in the security mode and which is used to reset the firing furnace or press furnace to an initial state in which free programming in the programming mode or free operation in the security mode is possible.

13. The firing furnace or press furnace according to claim 1, characterized in that the display device and/or input device comprises at least one symbol field for opening the firing furnace or press furnace and at least one symbol field for closing the firing furnace or press furnace, wherein the symbol fields for opening and closing the firing furnace or press furnace are active when no firing/press program is running.

14. The firing furnace or press furnace according to claim 1, characterized in that in addition to the security mode and a programming mode, a priority operating mode is selectable, by activating a selection field from the programming mode and/or by entering a code from the security mode in which a user can set further parameters, wherein setting further parameters comprises changing firing parameters and/or press parameters of programs temporarily, beyond functions of the security mode.

15. The firing furnace or press furnace according to claim 1, characterized in that a high security mode is selectable in which only one single firing/press program can be started and which can be left in the security mode, a priority operating mode and/or a programming mode by entering a code.

16. The firing furnace or press furnace according to claim 9, characterized in that the acoustic signal comprises a buzzing sound.

* * * * *